(12) United States Patent
Shalaby et al.

(10) Patent No.: US 6,794,485 B2
(45) Date of Patent: Sep. 21, 2004

(54) AMORPHOUS POLYMERIC POLYAXIAL INITIATORS AND COMPLIANT CRYSTALLINE COPOLYMERS THEREFROM

(75) Inventors: Shalaby W. Shalaby, Anderson, SC (US); Torbjorn Mathisen, Alvsjo (SE)

(73) Assignee: Poly-Med, Inc., Anderson, SC (US)

( * ) Notice: Subject to any disclaimer, the term of this patent is extended or adjusted under 35 U.S.C. 154(b) by 12 days.

(21) Appl. No.: 10/285,040

(22) Filed: Oct. 31, 2002

(65) Prior Publication Data

US 2003/0120029 A1 Jun. 26, 2003

Related U.S. Application Data (63) Continuation-in-part of application No. 10/003,640, filed on Nov. 2, 2001, which is a continuation-in-part of application No. 09/698,527, filed on Oct. 27, 2000, now Pat. No. 6,462,169.

(51) Int. Cl.$^7$ .................... C08G 63/08; C08G 69/08; A61B 17/00
(52) U.S. Cl. .................. 528/354; 528/355; 528/357; 528/358; 528/359; 525/408; 525/411; 525/413; 525/415; 606/228; 606/229; 606/230; 606/231; 623/1.15
(58) Field of Search ................. 528/354–355, 528/357–359; 525/408, 411, 413, 415; 606/228–231; 623/1.15

(56) References Cited

U.S. PATENT DOCUMENTS

| | | | |
|---|---|---|---|
| 3,797,499 A | * 3/1974 | Schneider | 606/230 |
| 4,429,080 A | 1/1984 | Casey et al. | 525/415 |
| 4,470,416 A | 9/1984 | Kafrawy et al. | 128/335.5 |
| 4,532,928 A | 8/1985 | Bezwada et al. | 128/335.5 |
| 4,543,952 A | 10/1985 | Shalaby et al. | 128/335.5 |
| 5,133,739 A | 7/1992 | Bezwada et al. | 606/230 |
| 5,236,444 A | 8/1993 | Muth et al. | 606/230 |
| 5,403,347 A | 4/1995 | Roby et al. | 606/230 |
| 5,431,679 A | 7/1995 | Bennett et al. | 606/230 |
| 5,468,253 A | 11/1995 | Bezwada et al. | 606/228 |
| 5,554,170 A | 9/1996 | Roby et al. | 606/230 |
| 5,620,461 A | 4/1997 | Muijs Van De Moer et al. | 606/213 |
| 5,644,002 A | 7/1997 | Cooper et al. | 525/411 |
| 5,713,920 A | 2/1998 | Bezwada et al. | 606/230 |
| 6,277,927 B1 | * 8/2001 | Roby et al. | 525/411 |
| 6,413,539 B1 | * 7/2002 | Shalaby | 424/426 |
| 6,462,169 B1 | 10/2002 | Shalaby | 528/354 |

FOREIGN PATENT DOCUMENTS

| | | | |
|---|---|---|---|
| EP | 0 618 250 A1 | 3/1994 | C08G/63/91 |
| EP | 0 697 427 A2 | 7/1995 | C08G/63/08 |
| EP | 0 712 880 A2 | 11/1995 | C08G/81/00 |
| EP | 0 737 703 A2 | 4/1996 | C08G/63/664 |

OTHER PUBLICATIONS

Correa et al., Sixth World Biomaterials Congress, *Trans So.c Biomat., II*, 992 (2000).
L. Mandelkern, *Crystallization of Polymers*, McGraw–Hill Book Company, NY, 1964, p. 105–106.
S.W. Shalaby, Chapter 3 of *Thermal Characterization of Polymeric Materials* (E.A. Turi ed.) Academic Press, NY, 1981, p. 330.
S.W. Shalaby and H.E. Blair, Chapter 4 of *Thermal Characterization of Polymeric Materials* (E.A. Turi ed.) Academic Press, NY, 1981, p. 402.

* cited by examiner

*Primary Examiner*—P. Hampton Hightower
(74) *Attorney, Agent, or Firm*—Leigh P. Gregory (57) ABSTRACT

An absorbable crystalline, monocentric polyaxial copolymer comprising a central carbon or nitrogen atom and at least three axes, each of which includes an amorphous flexible component adjacent and originating from the central atom and a rigid, crystallizable component extending outwardly from the amorphous, flexible component is disclosed along with the use of such copolymer in medical devices which may contain a bioactive agent. The present invention also relates to a suture, stents, stent mantles and sealing devices made from the polyaxial copolymer.

24 Claims, 2 Drawing Sheets

AMORPHOUS POLYMERIC POLYAXIAL INITIATORS AND COMPLIANT CRYSTALLINE COPOLYMERS THEREFROM

This is a continuation-in-part of U.S. Ser. No. 10/003,640, filed Nov. 2, 2001, which is a continuation-in-part of U.S. Ser. No. 09/698,527, filed Oct. 27, 2000, now U.S. Pat. No. 6,462,169.

FIELD OF THE INVENTION

The present invention generally relates to absorbable, crystalline, monocentric, polyaxial copolymers having a crystalline component, and a flexible, amorphous component. More specifically, the invention relates to such copolymers wherein the flexible and/or the crystalline component of the polymer comprise lactide units. The invention also relates to a method of producing such copolymers, and products thereof. The copolymers of the invention exhibit improved compliance, and prolonged mechanical integrity in vivo.

BACKGROUND OF THE INVENTION

Soft and pliable absorbable polymers are most often made as block or segmented copolymers consisting of an amorphous middle part and a terminal part having blocks or segments capable of crystallization. The amorphous middle part is made up of polyaxial chains, which result in a central component having a glass transition temperature below room temperature. The mobility of the polymer chains in the central component is thus high, and a relatively low mechanical force is required to displace segments of the polymer chains giving rise to the soft characteristics. The crystalline segments or blocks at the ends of each soft middle block or segment contribute to the overall material integrity and final mechanical strength. Such polymers made from linear initiators often possess a high percentage of crystalline phase and are often used in various suture materials where high mechanical strength are needed. However, in various soft and hard tissue applications where absorbable medical devices are sought for, the materials should preferably be as soft and pliable as possible to reduce the modulus mismatch between implant and tissue, which often can lead to unnecessary inflammatory response. One approach to further reduce the crystallinity and also the size of individual crystalline domains has been found to be to utilize tri- or tetra-functional initiators as previously disclosed in WO 0140348. Accordingly, WO 0140348 generally discloses absorbable, crystalline, monocentric, polyaxial copolymers having a crystalline component, and a flexible, amorphous component. The polymers can be prepared from a monomeric initiator, which is a tri- or tetra-functional organic compound, by reacting such initiator with at least one cyclic comonomer, selected from carbonates and lactones to form an amorphous polymeric, polyaxial initiator, and then reacting the amorphous, polymeric, polyaxial initiator with at least one lactone comprising a member selected from the group consisting of glycolide, lactide, p-dioxanone (1,4-dioxan-2-one), and combinations thereof. The copolymers are said to be crystallizable materials with melting temperatures above 100° C., which can be melt-processed into highly compliant absorbable films and fibers. The polymers are primarily intended for use in medical absorbable devices, such as, for example, stents, sutures, sealing devices for closing a wound in a wall of a blood vessel. Examples of the latter can be found in EP-B-1169968.

The present inventors have now surprisingly found that by using lactide in the amorphous core component and/or the crystalline hard block or segment of the polymers generally described in WO 0140348 certain desirable properties of the said polymers can be obtained. More particularly, the use of lactide as comonomer in the amorphous central core has been found to produce copolymers having markedly increased toughness; and when lactide is used in the crystalline terminals, it has been found to yield materials with modulated high ultimate elongation through controlling the degree of crystallinity and extent of phase mixing between the amorphous core and crystalline terminals without compromising the ability to retain the device integrity and its mechanical properties over a longer period of time.

SUMMARY OF THE INVENTION

According to the present invention, it has been found that by using L-lactide, with or without a small fraction of one or more cyclic monomer such as trimethylene carbonate, D,L-lactide, 1,4-dioxan-2-one, 1,5-dioxepan-2-one and caprolactone, in the hard terminal crystalline segment of the absorbable copolymers prepared from tri- or tetra-functional initiators, absorbable, compliant copolymers having high ultimate elongation can be obtained. This is especially advantageous in devices, which may be deformed during the surgical procedure or be exposed to dynamic movements after implantation. Furthermore, these materials exhibit an increased period of stability after implantation compared to similar materials where the hard crystalline segment is derived exclusively, or mostly, from glycolide. This is especially important in such applications where the material should act as a barrier to separate tissues where at least one of the tissues regenerates at slow speed compared to other adjacent tissues. An increased period of stability is also important from a biocompatibility point of view. When degradation starts shortly after implantation of the absorbable device, the degradation products, although non-toxic, may contribute to a more intense inflammation and also more scar tissue formation, which normally is an unwanted type of tissue regeneration. These copolymers will retain their mechanical properties over longer periods of time as compared to the similar polymers also when glycolide is used in the soft amorphous core.

The present inventors have also surprisingly found that by using a small amount of lactide in the amorphous segments, the copolymers will have a markedly reduced sensitivity to moisture, and thus improved storage life. It has also been found that such copolymers will exhibit prolonged mechanical retention in vitro and when stored in a humid environment. Thus, incorporation of D,L-lactide-based sequences in the amorphous core of about 2 percent, by mole, based on the overall composition of the copolymer is sufficient to produce the effects of the invention.

The copolymers of the invention especially find applicability in medical absorbable implants, wherein the material should possess high flexibility and also a low Young's modulus combined with a longer functional lifetime of the device in vivo.

Accordingly, in one aspect the present invention is directed to an absorbable, crystalline, monocentric, polyaxial copolymer exhibiting improved mechanical properties, having at least three axes originating and extending outwardly from the centre of the copolymer, which centre is formed from an at least tri- or tetra-functional initiator molecule, each axis including an amorphous, flexible component adjacent to and originating from the centre, the amorphous component being formed of repeat units derived from at least one cyclic monomer selected from the group consisting of carbonate and lactones, and a rigid, crystallizable component extending outwardly from the amorphous, flexible component, the crystallizable component being formed of repeat units derived from at least one lactone, wherein lactide is contained in at least one of said components of said copolymer.

In one embodiment, a copolymer exhibiting improved storage life and reduced sensitivity to moisture is provided, containing lactide in the amorphous component.

In another embodiment, a copolymer exhibiting high flexibility and elongation to break as well as prolonged period of stability after implantation and reduced sensitivity to moisture is provided, containing lactide in the crystalline component.

In a further embodiment, both components comprise lactide units, thus combining the characteristics of the two-lactide containing components.

According to another aspect the present invention relates to polymeric, polyaxial lactide-containing initiators (PPIs), from which PPIs the copolymers can be prepared.

In a further aspect the present invention relates to a method of preparing the present copolymers.

According to still another aspect of the present invention the subject copolymer is converted to different forms of absorbable stents, a tubular mantle (or cover) for stents, sutures, sealing devices or parts of multicomponent sealing devices for closing (or plugging) a wound or a needle hole in a wall of a blood vessel, such as described in e.g. EP-B-1169968.

Figure 3:
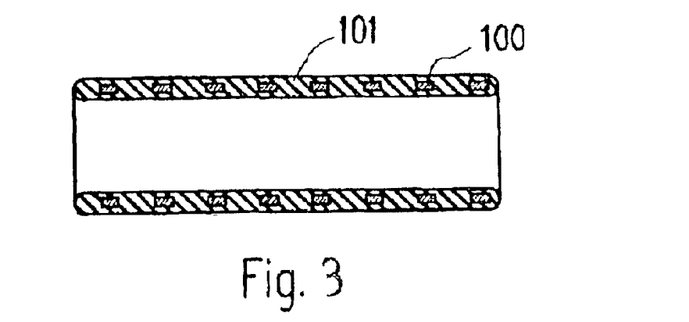
FIG. 3 is a longitudinal view of a stent 100 completely covered by the present copolymer.
Figure 4:
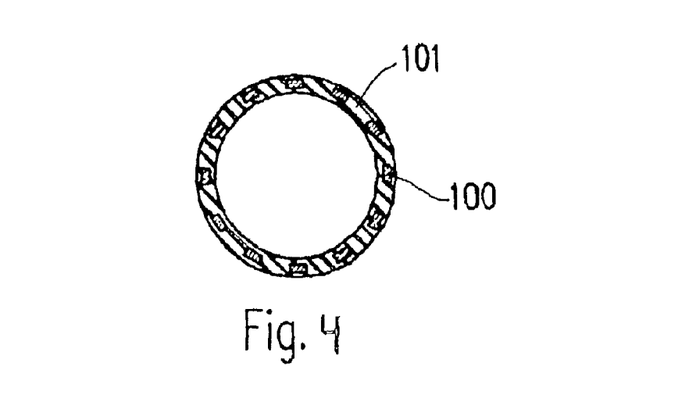
FIG. 4 is a cross sectional view of the stent shown in FIG. 2.
Figure 5:
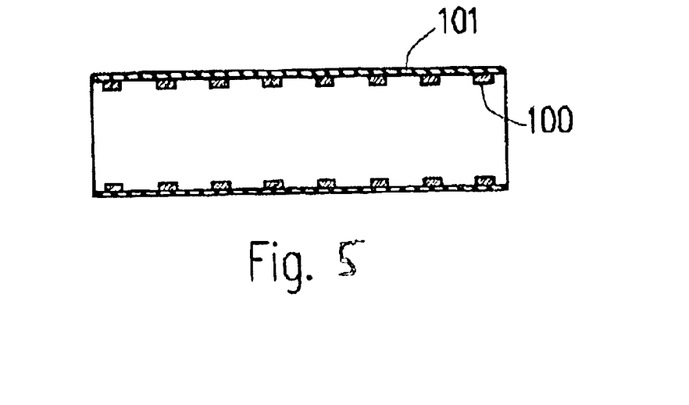
FIG. 5 is a longitudinal view of a stent 100 where the outer surface is covered by the subject copolymer 101.

In one embodiment, a composite cover or mantle (such as shown in FIGS. 3–5) for a stent which includes a polymeric matrix reinforced with monofilament cross-spirals may be provided, wherein the matrix, the monofilaments or both may be made of the copolymer of the present invention.

Figure 1:
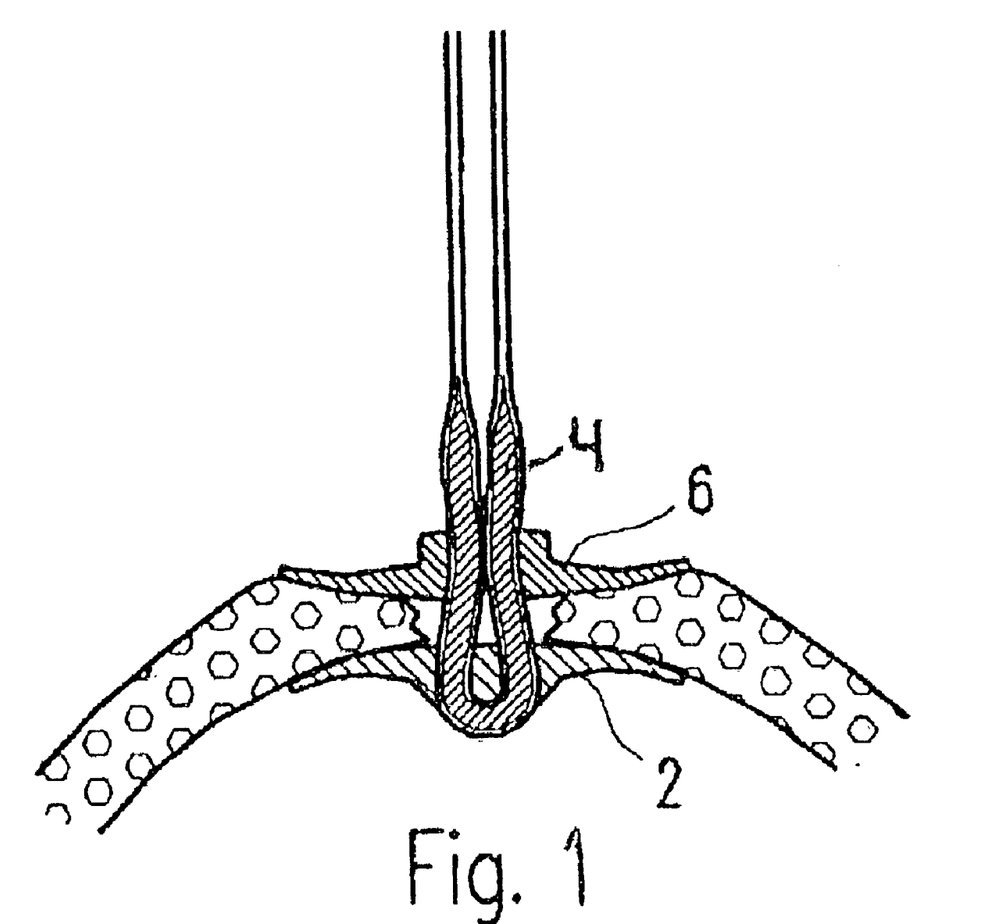
FIG. 1 illustrates a sealing device, having a first sealing member 2 to be positioned against the inner wall of a blood vessel, a second sealing member 6 to be positioned against the outer wall of the blood vessel, and an elongated member 4 that extends through the vessel wall and connects the first member to the second member.

In another embodiment the present invention is directed to a device for sealing a puncture in a blood vessel, such as shown in FIG. 1. The sealing device comprises basically a first sealing member to be positioned against the inner wall of a blood vessel, a second sealing member to be positioned against the outer wall of the blood vessel, and an elongated member that extends through the vessel wall and connects the first member to the second member.

Preferably, the first sealing member, the second sealing member, or both are formed from an absorbable polymer. Most preferably, at least one of the first sealing member and the second sealing member comprise an absorbable, crystalline, monocentric, polyaxial copolymer which includes a central atom selected from the group consisting of carbon and nitrogen; and at least three axes originating and extending outwardly from the central atom, each axis including: an amorphous, flexible component adjacent to and originating from the central atom, the amorphous component consisting of repeat units derived from at least one cyclic monomer selected from the group consisting essentially of carbonates and lactones; and a rigid, crystallizable component extending outwardly from the amorphous, flexible component, the crystallizable component consisting of repeat units derived from at least one lactone.

Preferably, the elongated member comprises a composite of a highly flexible sheath and a less flexible solid, monofilament core, the less flexible core within the sheath comprising the enlarged cross-sectional diameter of the distal locking portion of the elongated member composite. It is preferred that the sheath is a braided suture with a strength retention profile that exceeds those of other components of the device, and the less flexible filament is threaded through the interior portion of the suture. It is also preferred that the ends of the filament are tapered. In one embodiment the less flexible filament is sufficiently flexible to compress and frictionally engage the opening defined within the second sealing member.

Further embodiments and advantages will be evident to skilled reader from the following detailed description.

DETAILED DESCRIPTION AND PREFERRED EMBODIMENTS

According to the present invention, the lactide used in the amorphous component can be D,L-lactide, meso-lactide, L,L-lactide or D,D-lactide while the lactide used in the crystalline component is L,L- or D,D-lactide. This is an important requirement according to the present invention in order to obtain the desired properties of the respective components. Furthermore, glycolide and lactide should not be present in the same component of any given copolymer of the invention.

Preferred copolymers exhibit a melting temperature greater than 60° C. and preferably greater than 90° C., and most preferably greater than 120° C. and are characterized by a heat of fusion greater than 5 J/g. In the segmented copolymers where the crystalline component consists of glycolide, and to a lesser extent when the hard segment comprises lactide, an endothermic transition in the range 40–100° C. is found, wherein the endothermic transition can be controlled by subsequent heat treatment, such as orientation or annealing, of the copolymer. Depending on the process conditions and the subsequent heat treatment, the preferred copolymers typically have a Young's modulus that ranges from 2 to 200 MPa and an elongation at break of 100 to 1200% or above.

This invention deals with absorbable, polyaxial, monocentric, crystallizable, polymeric molecules with non-crystallizable, flexible components of the chain at the core and rigid, crystallizable segments at the chain terminals. One specific aspect of the present invention is directed to the design of lactide-containing amorphous polymeric polyaxial initiators with branches originating from a tri- or tetra-functional organic compound so as to extend along more than two coordinates and their subsequent end-grafting with cyclic monomers to produce compliant, crystalline film- and fiber-forming absorbable materials. The absorbable copolymeric materials of this invention comprise at least 30 percent, and preferably 65 percent, by mole, of a crystallizable component which is made primarily of glycolide-derived, lactide (L,L- or D,D-) derived or 1,4-dioxan-2-one sequences, and exhibit first and second order transitions below 222° C. and below 60° C., respectively, and undergo complete dissociation into water-soluble by-products.

Accelerated degradation in vitro at 70° C. in a phosphate buffer solution, kept at pH 7.4, shows after 7 days that when lactide is used in the hard segment, only about 5 percent weight loss of the material occurs, while about 60 percent weight loss occurs during the same period of time in a segmented copolymer having glycolide in the hard segment. As a comparison pure poly-D,L-lactide and poly-D,L-co-L, L-lactide (70:30) both have a weight loss of about 50 percent after the same time period. Both latter polymers are relatively hard and stiff and mainly used in orthopedic applications. It is clear that the segmented copolymer having lactide in the hard component as described here exhibits some very interesting properties compared to existing polymers. The increased stability after implantation together with the high elongation before break, as well as the flexibility characterized by the low modulus, is an especially sought for property when dealing with slow growing tissues and in a healing environment where the early release of degradation products could lead to increased inflammation and thus may compromise the early ongoing tissue regeneration.

The amorphous polymeric, polyaxial initiators (PPIs) used in this invention to produce crystalline absorbable copolymeric materials can be made by reacting a cyclic monomer or a mixture of cyclic monomers such as trimethylene carbonate, caprolactone, 1,5-dioxapan-2-one or 1,4-dioxan-2-one and a relatively small amount of lactide or glycolide in the presence of an organometallic catalyst with one or more polyhydroxy, polyamino, or hydroxyamino compound having three or more reactive amines and/or hydroxyl groups. Typical examples of the latter compounds are glycerol and ethane-trimethylol, propane-trimethylol, pentaerythritol, triethanolamine, and N-2-aminoethyl-1,3-propanediamine.

The flexible polyaxial initiator can be derived from any of the cyclic monomers trimethylene carbonate, caprolactone, 1,4-dioxane-2-one, 1,5-dioxepan-2-one in combination with glycolide or lactide. The polyaxial initiator can thus consist of one or two of the cyclic monomers trimethylene carbonate, caprolactone, 1,4-dioxane-2-one, 1,5-dioxepan-2-one in combination with glycolide or lactide. Especially for the monomers caprolactone and the 1,5-dioxepane-2-one, their cyclic dimers, 14 membered lactone rings, can be used instead of the respective monomers.

When used in the polyaxial initiator, L—L-lactide or D,D-lactide is present in a range preferably of between 2 and 10 mole percent, but more preferably in the range 3 to 7 mole percent. When D,L-lactide or meso-lactide is used in the polyaxial initiator the preferred range is between 2 and 25 mole percent, but more preferably 3 to 10 mole percent. The polyaxial initiator should furthermore have a glass transition temperature below 25° C. and more preferably below 15° C. when measured with Differential Scanning Calorimetry.

Further, the crystallizable block can be derived from glycolide, lactide, caprolactone or 1,4-dioxane-2-one. Alternative precursors of the crystalline component can be a mixture that is predominantly glycolide or lactide with a minor amount of one or more of the following monomers: 1,4-dioxane-2-one, 1,5-dioxepan-2-one, trimethylene carbonate, and caprolactone.

The crystalline copolymers of the present invention are so designed to (1) have the PPI devoid of any discernable level of crystallinity; (2) have the PPI component function as a flexible spacer of a terminally placed, rigid, crystallizable component derived from lactide, glycolide, caprolactone or 1,4-dioxane-2-one so as to allow for facile molecular entanglement to create pseudo-crosslinks, which in turn, maximize the interfacing of the amorphous and crystalline fractions of the copolymer leading to high compliance without compromising tensile strength; (3) maximize the incorporation of the glycolate or lactate linkage in the copolymer without compromising the sought high compliance—this is achieved by directing the polyglycolide or polylactide segments to grow on multiple active sites of the polymeric initiator and thus limiting the length of the crystallizable chain segments; (4) have a broad crystallization window featuring maximum nucleation sites and slow crystallite growth that in turn assists in securing a highly controlled post-processing and development of mechanical properties—this is achieved by allowing the crystallizable components to entangle effectively with non-crystallizable components leading to high affinity for nucleation, high pre-crystallization viscosity, slow chain motion, and low rate of crystallization; (5) force the polymer to form less perfect crystallites with broad size distribution and lower their melting temperature as compared to their homopolymeric crystalline analogs to aid melt-processing—this is achieved by limiting the length of the crystallizable segments of the copolymeric chain as discussed earlier; (6) allow for incorporating basic moieties in the PPI which can affect autocatalytic hydrolysis of the entire system which in turn accelerates the absorption rate; and (7) allow the polymer chain to associate so as to allow for endothermic thermal events to take place between 40 and 100° C. in the copolymers with more than 50 percent made of crystalline lactide- and/or glycolide-based terminal segments that can be associated with an increase in tensile toughness similar to that detected in PET relative to the so-called middle endothermic peak (MEP) (S. W. Shalaby, Chapter 3 of *Thermal Characterization of Polymeric Materials*, Academic press, NY, 1981, p. 330). The temperature at which these transitions take place is dependent on the degree of orientation of the polymers of this invention and the temperatures at which the polymers are annealed.

As an example, the crystalline copolymeric materials of the present invention may be prepared as follows, although as noted above, other monomers are also within the scope of the present invention. The amorphous polymeric polyaxial initiator is formed by a preliminary polymerization of a mixture of caprolactone and trimethylene carbonate in the presence of trimethylolpropane and a catalytic amount of stannous octanoate, using standard ring-opening polymerization conditions which entail heating the stirred reactants in nitrogen atmosphere at a temperature exceeding 110° C. until substantial or complete conversion of the monomers is realized. This can be followed by adding a predetermined amount of lactide. Following the dissolution of the lactide in the reaction mixture, the temperature is raised to 180° C. and kept for less than 30 minutes to allow the lactide to copolymerize with the polyaxial initiator without compromising the expected sequence distribution in PPI and the microtexture of the crystallizable terminal. The reaction is then continued at about 140° C. until practically all the lactide is reacted. The resulting copolymer is cooled then to 25° C. After removing the polymer from the reaction kettle and grinding, trace amounts of unreacted monomer are removed by heating under reduced pressure. The ground polymer can then be used as is or further extruded and pelletized prior to its conversion into fibers, films or any specially designed structure by conventional melt or solvent based processing methods. At the appropriate stage of polymerization and product purification, traditional analytical methods, such as gel-permeation chromatography (GPC), solution viscosity, differential scanning calorimetry (DSC), nuclear magnetic resonance (NMR), and infrared spectroscopy (IR) are used to monitor or determine (directly or indirectly) the extent of monomer conversion, molecular weight, thermal transitions (melting temperature, $T_m$, and glass transition temperature, $T_g$), chain microstructure, and chemical entity, respectively.

As previously mentioned, another aspect of this invention deals with end-grafting a PPI with 1,4-dioxane-2-one, caprolactone or lactide, and preferably in the presence of a minor amount of a second monomer, to produce absorbable crystalline polymers for use as bone sealants, sealants for synthetic vascular grafts, as well as modifiers to increase the toughness and tear strength of synthetic vascular grafts, matrices for the controlled release of bioactive agents for modulating biological events in and about synthetic vascular grafts, endovascular stents, or stent mantles (or covers), barrier membranes, thin films, or sheets. The latter four forms of the crystalline polymers can be made to have continuous-cell microporous morphology.

Films made by compression molding of the copolymers described in the examples set forth below are evaluated for (1) tensile strength; (2) in vitro breaking strength retention and mass loss during incubation in a phosphate buffer at 37° C. and 70° C. and pH 7.4.

Specifically, an important aspect of this invention is the production of compliant absorbable films with modulated absorption and strength loss profiles to allow their use in a wide range of applications as vascular devices such as stent cover or mantel or components therefore. More specifically is the use of these devices in sealing punctured blood vessels.

In another aspect, this invention is directed to the use of the polymers described herein for the production of extruded or molded films for use in barrier systems to prevent post-surgical adhesion or compliant covers, sealants, or barriers for burns and ulcers as well as compromised/damaged tissue. The aforementioned articles may also contain one or more bioactive agent to augment or accelerate their functions. In another aspect, this invention is directed to melt-processed films for use as a patch (or a component of a patch) for repairing mechanically compromised blood vessels. In another aspect, this invention is directed to the use of the polymer described herein as a coating for intravascular devices such as catheters. In another aspect, this invention is directed to the application of the polymers described herein in the production of extruded catheters for use as transient conduits and microcellular foams with continuous porous structure for use in tissue engineering and guiding the growth of blood vessels and nerve ends. Another aspect of this invention is directed to the use of the polymers described herein to produce injection molded articles for use as barriers, or plugs, to aid the function of certain biomedical devices used in soft and hard tissues and which can be employed in repairing, augmenting, substituting or redirecting/assisting the functions of several types of tissues including bone, cartilage, and lung as well as vascular tissues and components of the gastrointestinal and urinogenital systems. In another aspect, this invention is directed to the use of polymers described herein to produce compliant, melt-blown fabrics and monofilament sutures with modulated absorption and strength retention profiles.

In one aspect of this invention, the subject copolymers are converted to different forms of absorbable stents, such as those used (1) as an intraluminal device for sutureless gastrointestinal sutureless anastomosis; (2) in laparoscopic replacement of urinary tract segments; (3) as an intraluminal device for artery welding; (4) in the treatment of urethral lesions; (5) as a tracheal airway; (6) in the treatment of recurrent urethral strictures; (7) for vasectomy reversal; (8) in the treatment of tracheal stenosis in children; (9) for vasovasostomy; (10) for end-to-end ureterostomy; and (11) as biliary devices.

In another aspect of this invention, the subject copolymers are converted to a highly compliant, expandable tubular mantle, sleeve or cover that is placed tightly outside an expandable metallic or polymeric stent so that under concentric irreversible expansion at the desired site of a treated biological conduit, such as blood vessel or a urethra, both components will simultaneously expand and the mantle provides a barrier between the inner wall of the conduit and the outer wall of the stent. In another aspect of this invention, the subject copolymers are used as a stretchable matrix of a fiber-reinforced cover, sleeve, or mantle for a stent, wherein the fiber reinforcement is in the form of spirally coiled yarn (with and without crimping) woven, knitted, or braided construct. In another aspect of this invention, the stent mantle, or cover, is designed to serve a controlled release matrix of bioactive agents such as those used (1) for inhibiting neointima formation as exemplified by, but not limited to, hirudin and the prostacyclic analogue, iloprost; (2) for inhibiting platelet aggregation and thrombosis; (3) for reducing intraluminal and particular intravascular inflammation as exemplified by dexamethasone and non-steroidal inflammatory drugs, such as naproxen; and (4) for suppressing the restenosis.

One aspect of this invention deals with the conversion of the subject copolymers into molded devices or components of devices used as a hemostatic puncture closure device after coronary angioplasty.

It is further within the scope of this invention to incorporate one or more medico-surgically useful substances into the copolymers and devices subject of this invention. Typical examples of these substances are those capable of (1) minimizing or preventing platelet adhesion to the surface of vascular grafts; (2) rendering anti-inflammatory functions; (3) blocking incidents leading to hyperplasia as in the case of synthetic vascular grafts; (4) aiding endothelialization of synthetic vascular grafts; (5) preventing smooth muscle cell migration to the lumen of synthetic vascular grafts; and (6) accelerating guided tissue ingrowth in fully or partially absorbable scaffolds used in vascular tissue engineering.

In order that those skilled in the art may be better able to practice the present invention, the following illustrations of the preparation of typical crystalline copolymers are provided.

EXAMPLE 1

Synthesis of 21/30/4 (Molar) Caprolactone (CL)/ Trimethylene Carbonate (TMC)/Glycolide (G) as a Triaxial Polymeric Initiator and Reaction with 40/5 Relative Molar Parts of L,L-Lactide (LLA)/CL To produce the triaxial polymeric initiator, glycolide (22.74 g, 0.2 mole), trimethylene carbonate (149.94 g, 1.47 mole), caprolactone (117.31 g, 1.03 mole), triethanolamine (1.34 g, 9 mmole), and stannous octoate ($3.86 \times 10^{-4}$ mole as 0.2M solution in toluene) were reacted under nitrogen in a pre-dried reactor equipped with a mechanical stirrer. The formation of the polymeric triaxial initiator was completed after heating at 180° C. for 125 minutes with constant mixing. The product was cooled to room temperature and a mixture of L-lactide (282.24 g, 1.96 mole) and caprolactone (27.98 g, 0.25 mole) were added under nitrogen atmosphere. The end-grafting to produce the crystalline segmented copolymer was accomplished after heating between 195–200° C. for 5 minutes and then for 24 hours at 140° C. The resulting polymer was isolated, pulverized, dried and heated under reduced pressure to remove residual monomer. The polymer was characterized by NMR and IR (for identity), DSC for thermal transitions ($T_m$=148° C., $\Delta H$=19 J/g), and inherent viscometry (I.V.) in chloroform (for molecular weight, I.V.=1.14 dL/g).

EXAMPLE 2

Synthesis of 25/25 (Molar) CL/TMC as a Triaxial Polymeric Initiator and Reaction with 45/5 Relative Molar Parts of LLA/TMC The triaxial polymeric initiator was prepared using trimethylene carbonate (141.8 g, 1.39 mole), caprolactone (158.5 g, 1.39 mole), triethanolamine (1.38 g, 9 mmole), and Stannous Octoate ($3.97 \times 10^{-4}$ mole as 0.2M solution in toluene) and following a similar reaction scheme as described in Example 1. Similarly, the end-grafting to produce the crystalline segmented copolymer was performed using L-lactide (277.92 g, 1.93 moles) and trimethylene carbonate (21.9 g, 0.215 moles). The resulting polymer was characterized by NMR and IR (for identity), DSC for thermal transitions ($T_m$=150° C., $\Delta H$=6.7 J/g), and inherent viscometry (I.V.) in chloroform (for molecular weight, I.V.=0.85 dL/g).

EXAMPLE 3

Synthesis of 22/3/31 (Molar) CL/G/TMC as a Triaxial Polymeric Initiator and Reaction with 40/4 Relative Molar Parts of LLA/CL The triaxial polymeric initiator was prepared using glycolide (17.07 g, 0.147 moles) trimethylene carbonate (155.07 g, 1.52 mole), caprolactone (122.99 g, 1.08 mole), triethanolamine (1.37 g, 9 mmole), and stannous octoate ($3.92 \times 10^{-4}$ mole as 0.2M solution in toluene) and following a similar reaction scheme as described in Example 1. Similarly, the end-grafting to produce the crystalline segmented copolymer was performed using L-lactide (282.24 g, 1.96 moles) and caprolactone (22.36 g, 0.196 moles). The resulting polymer was characterized by NMR and IR (for identity), DSC for thermal transitions ($T_m$=159° C., $\Delta H$=18 J/g), and inherent viscometry (I.V.) in chloroform (for molecular weight, I.V.=1.29 dL/g).

EXAMPLE 4

Synthesis of 25/25 (Molar) CL/TMC as a Triaxial Polymeric Initiator and Reaction with 45/5 Relative Molar Parts of LLA/CL The triaxial polymeric initiator was prepared using trimethylene carbonate (141.8 g, 1.39 mole), caprolactone (158.5 g, 1.39 mole), triethanolamine (0.691 g, 4.6 mmole), and stannous octoate ($3.97 \times 10^{-4}$ mole as 0.2M solution in toluene) and following a similar reaction scheme as described in Example 1. Similarly, the end-grafting to produce the crystalline segmented copolymer was performed using L-lactide (275.8 g, 1.92 moles) and trimethylene carbonate (24.26 g, 0.213 moles). The resulting polymer was characterized by NMR and IR (for identity), DSC for thermal transition ($T_m$=161° C., $\Delta H$=9.2 J/g), and inherent viscometry (I.V.) in chloroform (for molecular weight, I.V.=1.61 dL/g).

EXAMPLE 5

Synthesis of 26/26/4 (Molar) CL/TMC/G as a Triaxial Initiator and Reaction with 40/4 Relative Molar Parts of LLA/CL The triaxial polymeric initiator was prepared using glycolide (11.32 g, 0.98 moles), trimethylene carbonate (64.7 g, 0.634 mole), caprolactone (72.32 g, 0.634 mole), triethanolamine (0.51 g, 3.4 mmole), and stannous octoate ($1.37 \times 10^{-4}$ mole as 0.2M solution in toluene) and following a similar reaction scheme as described in Example 1. Similarly, the end-grafting to produce the crystalline segmented copolymer was performed using L-lactide (140.54 g, 0.98 moles), and caprolactone (11.13 g, 0.098 moles). The polymer was characterized by NMR and IR (for identity), DSC for thermal transition ($T_m$=135° C., $\Delta H$=15 J/g), and inherent viscometry (I.V.) in chloroform (for molecular weight, I.V.=1.28 dL/g).

EXAMPLE 6

Synthesis of 25/25 (Molar) CL/TMC as a Polymeric Triaxial Initiator and Reaction with 50 Relative Molar Parts of LLA The triaxial initiator was prepared using trimethylene carbonate (61.2 g, 0.6 mole), caprolactone (68.4 g, 0.6 mole), triethanolamine (0.51 g, 3.4 mmole), and stannous octoate ($1.37 \times 10^{-4}$ mole as 0.2M solution in toluene), and following a similar reaction scheme as described in Example 1. Similarly, the end-grafting to produce the crystalline segmented copolymer was performed by using L-lactide (172.8 g, 1.2 mole). The resulting polymer was characterized by NMR and IR (for identity), DSC for thermal transitions ($T_m$=150° C., $\Delta H$=20 J/g), and an inherent viscosity (I.V.) in chloroform (for molecular weight, I.V.=1.36 dL/g).

EXAMPLE 7

Synthesis of 13.6/17.0/2.0 (Molar) Caprolactone/ Trimethylene Carbonate/D,L-Lactide Copolymer as a Basic Polymeric Triaxial Initiator and Reaction with Relative 67.4 Molar Parts of Glycolide and Trimethylene Carbonate D,L-lactide (3.8 g, 0.0267 mole), TMC (23.0 g, 0.2255 mole), caprolactone (20.5 g, 0.1798 mole), triethanolamine (0.6775 g, 4.55 mmole) and stannous octoate catalyst (0.2M in toluene, 519 µL, 0.1038 mmole) were added under dry nitrogen conditions to a 0.5 Liter stainless steel reaction kettle equipped with a glass top and a mechanical stirrer. The reactants were melted at 85° C. and the system was evacuated with vacuum. The system was purged with dry nitrogen and the melt was heated to 160° C. with stirring at 30 rpm. Samples of the prepolymer melt were taken periodically and analyzed for monomer content using GPC. Once the monomer content of the melt was found to be negligible, glycolide (103.4 g, 0.8914 mole) was added with rapid stirring. The stir rate was lowered to 30 rpm after the contents were well mixed. The melt was heated to 180° C. Stirring was stopped upon solidification of the polymer. The polymer was heated for 2 hours at 180° C. after solidification. The resulting polymer was cooled to room temperature, quenched in liquid nitrogen, isolated, and dried under vacuum. The polymer was characterized for identity and composition (IR and NMR, respectively) and thermal transition by DSC ($T_m$=220° C.) and molecular weight by solution viscometry (η=0.80 in hexafluoroisopropyl alcohol).

EXAMPLE 8

Synthesis of 13.6/17.0/2.0 (Molar) Caprolactone/ Trimethylene Carbonate/D,L-Lactide Copolymer as a Polymeric Triaxial Initiator and Reaction with Relative 67.4 Molar Parts of Glycolide and Trimethylene Carbonate D,L-lactide (3.8 g, 0.0267 mole), TMC (23.0 g, 0.2255 mole), caprolactone (20.5 g, 0.1798 mole), trimethylolpropane (0.61 g, 4.55 mmole) and stannous octoate catalyst (0.2M in toluene, 519 μL, 0.1038 mmole) were added under dry nitrogen conditions to a 0.5 Liter stainless steel reaction kettle equipped with a glass top and a mechanical stirrer. The reactants were melted at 85° C. and the system was evacuated with vacuum. The system was purged with dry nitrogen and the melt was heated to 160° C. with stirring at 30 rpm. Samples of the prepolymer melt were taken periodically and analyzed for monomer content using GPC. Once the monomer content of the melt was found to be negligible, glycolide (103.4 g, 0.8914 mole) was added with rapid stirring. The stir rate was lowered to 30 rpm after the contents were well mixed. The melt was heated to 180° C. Stirring was stopped upon solidification of the polymer. The polymer was heated for 2 hours at 180° C. after solidification. The resulting polymer was cooled to room temperature, quenched in liquid nitrogen, isolated, and dried under vacuum. The polymer was characterized for identity and composition (IR and NMR, respectively) and thermal transition by DSC ($T_m$=219° C.) and molecular weight by solution viscometry (η=0.92 in hexafluoroisopropyl alcohol).

EXAMPLE 9

Size Reduction and Extrusion of Polymer from Examples 7 and 8

The polymer was quenched with liquid nitrogen and mechanically ground. The ground polymer was dried under vacuum at 25° C. for two hours, at 40° C. for two hours, and at 80° C. for four hours. The polymer was melt extruded at 235° C. to 245° C. using a ½ inch extruder equipped with a 0.094 in die. The resulting monofilament was quenched in an ice-water bath and jet-stretched to achieve the desired diameter for formation of cross-spirals (spirally coiled yarn) as described in the subsequent example. The monofilament was dried at 40° C. and under vacuum for four hours prior to use.

EXAMPLE 10

General Method for Assembling Composite Stent Mantle

The undrawn microfilaments from Example 9 were wrapped in two opposite directions on a Teflon rod having a diameter of 2–4 mm to provide a two-component, cross-spiral construct. Each constituent spiral was comprised of 1 to 10 turns/cm along the axis of the Teflon rod. While on the Teflon rod, the cross-spiral construct was coated with a solution (10–20% in dichloromethane, DCM) of the copolymer of Example 1. The coating process entails multiple steps of dipping and air-drying and was pursued until the desirable coating thickness is achieved (25–50 μl). Complete removal of the solvent was achieved by replacing the composite on the Teflon rod under reduced pressure at 25° C. for 6–12 hours until a constant weight is realized. The composite tube (typically 2–5 cm long) was removed from the Teflon cylinder by gentle sliding. This was then cut to the desired length before sliding over a metallic stent.

EXAMPLE 11

Comparative In Vitro Absorption Data of Typical Polymers of this Invention and Relevant Commercial Polymers The polymer (designated RD7) as in Example 1 of the prior art and described in WO 0140348 was compression molded using a temperature of 198° C. and a ram force of 70 kN to produce the first sealing member as described elsewhere (WO 0140348). Three other materials were also used: a triaxial segmented copolymer where the soft segment consists of caprolactone/trimethylene carbonate/ glycolide (25/20/5 mole %] and the hard segment consists of glycolide 50 mole % [STM2]; a commercial grade of poly-D,L-lactide [PDLA]; and a commercial grade of poly- D,L-co-L-lactide, 70:30, [PDL-co-LLA]. The first material was compression molded at 198° C., and the two latter materials at 150° C. and a ram force of 70 kN.

All materials were incubated at 70° C. in a phosphate buffer solution adjusted to pH 7.4. The buffer solution is described in the international standard ISO 13781. The pH of the buffer was kept constant during the test by periodic replacement. Samples were harvested after 2, 4, 7, 12, 20, 40, 60 and 100 days, washed in reverse osmosis water and dried for 5 days in vacuum. The weight loss was determined gravimetrically and the result is shown in the table below.

| Days | RD7 | STM2 | PDLA | PDL-co-LLA 70:30:00 |
|---|---|---|---|---|
| 0 | | | | |
| 2 | −16.7 | −3.0 | −0.9 | −1.3 |
| 4 | −40.6 | −4.6 | −3.5 | −5.5 |
| 7 | −59.3 | −6.2 | −53.3 | −49.7 |
| 12 | −71.3 | −11.9 | −92.2 | −63.6 |
| 20 | −80.4 | −21.9 | −98.9 | −72.2 |
| 40 | −94.9 | −44.5 | | −97.2 |
| 60 | −100.3 | −72.8 | | −101.2 |
| 80 | | −86.0 | | |
| 100 | | −96.1 | | |

EXAMPLE 12 (COMPARATIVE)

Synthesis of 20/25/5 (Molar) Caprolactone/ Trimethylene Carbonate/Glycolide Copolymer as a Polymeric Triaxial Initiator and Reaction with 50 Relative Molar Parts of Glycolide An initial charge consisted of 101.6 g (0.891 moles) caprolactone, 113.5 g (1.113 moles) trimethylene carbonate, 25.9 g of glycolide (0.223 moles), 1.996 g ($1.49 \times 10^{-2}$ moles) trimethylolpropane, and 1.0 ml ($1.28 \times 10^{-4}$ moles) of a 0.128M solution of stannous octoate catalyst in toluene after flame drying the reaction apparatus. The reaction apparatus was a 1 L stainless steel kettle with 3-neck glass lid equipped, an overhead mechanical stirring unit, vacuum adapter, and two 90° connectors for an argon inlet.

The apparatus and its contents were then heated to 85° C. under vacuum with a high temperature oil bath. After 30 minutes, with the contents completely melted, the system was purged with argon, stirring initiated at 34 rpm, and the temperature set to 140° C. After 4 hours at 140° C., 268.8 g (2.317 moles) of glycolide were added to the system while rapidly stirring. When the glycolide had completely melted and mixed into the polyaxial polymeric initiator, the temperature was increased to 180° C. and stirring was stopped. The reaction was allowed to continue for 2 hours before cooling the system to room temperature overnight. The polymer was isolated, ground, and dried as discussed in Example 1.

The polymer was characterized to provide the following data: The inherent viscosity using HFIP as a solvent was 0.93 dL/g. The melting temperature and heat of fusion, as measured by differential scanning calorimetry (DSC using initial heating thermogram), were 215° C. and 35 J/g, respectively.

EXAMPLE 13

Synthesis of 20/25/5 (Molar) Caprolactone/
Trimethylene Carbonate/D,L-Lactide Copolymer as
a Polymeric Triaxial Initiator and Reaction with 50
Relative Molar Parts of Glycolide An initial charge consisted of 101.6 g (0.891 moles) caprolactone, 113.5 g (1.113 moles) trimethylene carbonate, 32.1 g of D,L-lactide (0.223 moles), 1.996 g ($1.49 \times 10^{-2}$ moles) trimethylolpropane, and 1.0 ml ($1.28 \times 10^{-4}$ moles) of a 0.128M solution of stannous octoate catalyst in toluene after flame drying the reaction apparatus. The reaction apparatus was a 1 L stainless steel kettle with 3-neck glass lid equipped, an overhead mechanical stirring unit, vacuum adapter, and two 90° connectors for an argon inlet.

The apparatus and its contents were then heated to 85° C. under vacuum with a high temperature oil bath. After 30 minutes, with the contents completely melted, the system was purged with argon, stirring initiated at 34 rpm, and the temperature set to 140° C. After 4 hours at 140° C., 268.8 g (2.317 moles) of glycolide were added to the system while rapidly stirring. When the glycolide had completely melted and mixed into the polyaxial polymeric initiator, the temperature was increased to 180° C. and stirring was stopped. The reaction was allowed to continue for 2 hours before cooling the system to room temperature overnight. The polymer was isolated, ground, and dried as discussed in Example 1.

The polymer was characterized to provide the following data: The inherent viscosity using HFIP as a solvent was 0.96 dL/g. The melting temperature and heat of fusion, as measured by differential scanning calorimetry (DSC using initial heating thermogram), were 216° C. and 33 J/g, respectively.

EXAMPLE 14

In Vitro Mechanical Strength Retention Data of
Typical Crystalline Segmented Copolymers Dumbell shaped test specimens from the material described in Examples 12 and 13 of the present invention, wherein the soft segment consists of caprolactone/trimethylene carbonate/glycolide (25/20/5 mole %] and caprolactone/trimethylene carbonate/lactide (25/20/5 mole %], respectively, while the hard segment consists of glycolide [50 mole %] for both copolymers. The two polymers have been polymerized the same way.

A number of specimens were subjected to in vitro degradation in a phosphate buffer solution kept at pH 7.4 and 37° C. The buffer solution is described in the international standard ISO 13781. Test specimens were harvested after 4, 7 and 10 days for tensile testing. Samples having lactide in the soft block (polymer according to Example 1) display a retention of breaking strength of 80, 71 and 54 percent, respectively, whereas samples having glycolide in the soft block display a retention of breaking strength of 75, 60 and 43 percent, respectively. The data clearly show the increased stability when glycolide is substituted with lactide.

EXAMPLE 15

Mechanical Strength Retention at 75 Percent RH

Dumbell shaped test specimens from the material described in Examples 12 and 13 where the polymeric triaxial initiator contains for the respective crystalline polymers contained glycolide and D,L-lactide, respectively. This experiment was designed to compare the effect of the composition of the amorphous core of the polyaxial crystalline polymers having identical crystalline hard segments on their mechanical strength retention profiles.

A number of specimens were stored in a humid atmosphere, 75% RH at 25° C. Test specimens were harvested after 7 and 14 days for tensile testing. Samples having lactide in the soft segment (polymer of Example 13) display a retention of breaking strength of 100 and 100%, respectively, whereas samples having glycolide in the soft segment (polymer of Example 12) display a retention of breaking strength of 87 and 86%, respectively. The data clearly show the increased stability when glycolide is substituted with lactide.

Figure 2:
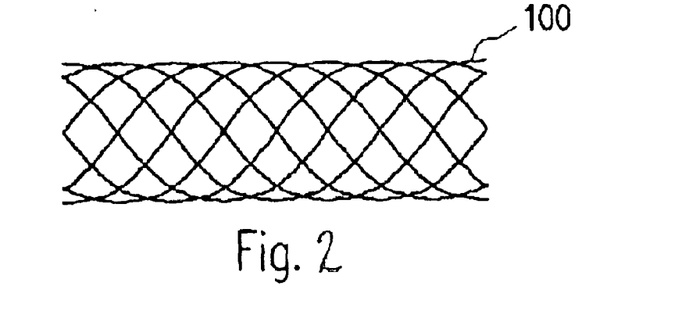
FIG. 2 shows schematically a radially expandable prior art spirally coiled metal stent 100 which is applicable in the present invention.

As mentioned above, the subject copolymers may be converted to a highly compliant, expandable tubular mantle, sleeve or cover that is placed tightly outside an expandable metallic or polymeric stent so that under concentric irreversible expansion at the desired site of a treated biological conduit, such as blood vessel or a urethra, both components will simultaneously expand and the mantle provides a barrier between the inner wall of the conduit and the outer wall of the stent. In another aspect of this invention, the subject copolymers are used as a stretchable matrix of a fiber-reinforced cover, sleeve, or mantle for a stent, wherein the fiber reinforcement is in the form of spirally coiled yarn (with or without crimping) woven, knitted, or braided construct. FIG. 2 shows schematically a radially expandable prior art spirally coiled metal stent which is applicable in the present invention.

FIG. 3 is a longitudinal view of a stent where the metal stent 100 is completely covered by the subject copolymer 101 according to a preferred embodiment of the present invention.

FIG. 4 is a cross sectional view of the stent shown in FIG. 2.

FIG. 5 is a longitudinal view of a stent where the outer surface is covered by the subject copolymer 101 according to another preferred embodiment of the present invention. The size of a stent depends naturally of the intended use, i.e. the dimensions of the vessel where it should be applied. Typical coronary stent dimensions may have a pre deployment outer diameter of 1.6 mm and an expanded outer diameter of 2.5 mm to 4.5 mm. The length is preferably 10 mm or 40 mm.

Although the present invention has been described in connection with the preferred embodiments, it is to be understood that modifications and variations may be utilized without departing from the principles and scope of the invention, as those skilled in the art will readily understand. Accordingly, such modifications may be practised within the scope of the following claims. Moreover, Applicants hereby disclose all subranges of all ranges disclosed herein. These subranges are also useful in carrying out the present invention.

What is claimed is:

1. An absorbable, crystalline, monocentric, polyaxial copolymer having improved mechanical characteristics and hydrolytic stability comprising:
    at least three axes originating and extending outwardly from the center of the copolymer, said center being formed from an at least tri-functional initiator molecule, each axis comprising:
        an amorphous, flexible component adjacent to and originating from the center, said flexible component comprising repeat units derived from at least one cyclic monomer selected from the group consisting essentially of carbonates and lactones; and
        a rigid, crystallizable component extending outwardly from the amorphous, flexible component, said crystallizable component being formed of repeat units derived from at least one lactone,
    characterized in that lactide is contained in at least one of said two components while glycolide is excluded from said at least one component.

2. The copolymer set forth in claim 1 wherein the amorphous component comprises a lactide selected from the group consisting essentially of L,L-lactide and D,D-lactide in an amount in the range of from 2 to 10 mole percent based on the total amount of monomers in the copolymer.

3. The copolymer set forth in claim 2 wherein the crystallizable component comprises repeat units derived from a lactide selected from the group consisting essentially of D,D-lactide and L,L-lactide, in amount of at least 30% by mole of the total copolymer.

4. The copolymer of claim 2 wherein the crystallizable component comprises repeat units derived from glycolide.

5. The copolymer of claim 2 wherein the crystallizable component comprises repeat units derived from a member selected from the group consisting essentially of caprolactone and 1,4-dioxan-2-one.

6. The copolymer of claim 1 wherein the crystallizable component comprises repeat units derived from a second monomer selected from the group consisting of trimethylene carbonate, caprolactone, 1,4-dioxan-2-one, and 1,5-dioxepan-2-one.

7. The copolymer of claim 1 wherein the amorphous component comprises units derived from glycolide.

8. The copolymer of claim 1 wherein the amorphous component comprises repeat units derived from a second monomer selected from the group consisting of trimethylene carbonate, caprolactone and dimers thereof, 1,4-dioxane-2-one, and 1,5-dioxepan-2-one and dimers thereof.

9. The copolymer set forth in claim 1 wherein the copolymer exhibits a melting temperature greater than 60° C., and a heat of fusion greater than 5 J/g copolymer.

10. The copolymer of claim 1 wherein the copolymer is subjected to heat treatment comprising orientation.

11. The copolymer of claim 1 wherein the copolymer is subjected to heat treatment comprising annealing above 25° C.

12. The copolymer of claim 1 comprising a Young's modulus in a range from 2 to 200 MPa, and on elongation at break of 100 to 1200%.

13. A method of preparing an absorbable, crystalline, monocentric, polyaxial copolymer having improved mechanical properties, comprising the steps of:
    (A) reacting at least one a cyclic monomer selected from the group consisting of trimethylene carbonate, caprolactone, and 1,5-dioxapane-2-one in the presence of an organometallic catalyst with at least one compound selected from the group consisting of polyhydroxy compounds, polyamino compounds, and hydroxyamino compounds, wherein the compound has at least three reactive amines and/or hydroxyl groups, to form an amorphous polymeric polyaxial initiator; and
    (B) reacting the amorphous, polymeric, polyaxial initiator with at least one monomer selected from the group consisting of glycolide, lactide, caprolactone and 1,4-dioxan-2-one.

14. The method of claim 13 further comprising the step of heat treating the copolymer.

15. A polymeric, polyaxial initiator, having at least three axes originating and extending outwardly from the center of the initiator, said center being formed from an at least tri-functional initiator molecule, each axis comprising:
    an amorphous, flexible component adjacent to and originating from the center, said flexible component comprising repeat units derived from at least one cyclic monomer selected from the group consisting essentially of carbonates and lactones, the initiator comprising lactide.

16. A medical device made from the polymer of claim 1 wherein the device is adapted to be implanted in a living body in close apposition to soft or hard tissue.

17. A device as set forth in claim 16 wherein the device as a whole or in part is porous.

18. A device as set forth in claim 16 wherein the device is adapted for sealing a puncture in a blood vessel and comprises a first sealing member adapted to be positioned against an inner surface of a blood vessel.

19. A device as set forth in claim 18 wherein the device further comprises a second sealing member adapted to be positioned against an outer surface of a blood vessel.

20. A composite tubular cover or mantle for a stent comprising a polymeric matrix reinforced with monofilament cross-spirals, wherein at least one of the matrix and the reinforcement comprise the copolymer of claim 1.

21. A composite tubular cover or mantle for a stent as set forth in claim 20 wherein the matrix is microporous.

22. A composite tubular cover or mantle for a stein as set forth in claim 20 wherein the matrix comprises a bioactive agent for prolonging the stent functional performance.

23. The copolymer set forth in claim 2 wherein the amorphous component comprises D,L-lactide in an amount in the range of from 2 to 25 mole percent based on the total amount of monomers in the copolymer.

24. A method of preparing an absorbable, crystalline, monocentric, polyaxial copolymer as set forth in claim 13 wherein step (A) further comprises reacting from about 0.5 to about 5.0 percent by weight of a second monomer selected from the group consisting of glycolide and 1-lactide with the at least one cyclic monomer and at least one compound, wherein the at least one monomer of step (B) comprises a monomer selected from the group consisting of glycolide and lactide, and wherein step (B) further comprises reacting from about 0.5 to about 5.0 percent by weight of a second monomer selected from the group consisting of 1,5-dioxepane-2-one, trimethylene carbonate, and caprolactone.

* * * * *